United States Patent [19]
Lojek

[11] Patent Number: 5,888,938
[45] Date of Patent: Mar. 30, 1999

[54] HERBICIDAL COMPOSITION AND USE

[75] Inventor: John S. Lojek, Elmira, Canada

[73] Assignee: Ecoval Inc., Montreal, Canada

[21] Appl. No.: 881,666

[22] Filed: Jun. 24, 1997

Related U.S. Application Data

[63] Continuation-in-part of Ser. No. 736,683, Oct. 25, 1996, Pat. No. 5,705,455, which is a continuation-in-part of Ser. No. 190,201, Jul. 18, 1994, Pat. No. 5,573,997.

[51] Int. Cl.⁶ .................................................. A01N 37/02
[52] U.S. Cl. .............................................................. 504/142
[58] Field of Search ................................................ 504/142

[56] References Cited

U.S. PATENT DOCUMENTS 3,869,377  3/1975  Berger et al. ............................ 71/113
4,529,797  7/1985  Peik et al. ................................ 536/123

FOREIGN PATENT DOCUMENTS 4030687  5/1991  Germany.

OTHER PUBLICATIONS

Abstract of JP 62-176922 (1987).

*Primary Examiner*—S. Mark Clardy
*Attorney, Agent, or Firm*—Sim & McBurney

[57] ABSTRACT

A herbicidal composition, which can be formulated for selective or total kill of vegetation or as a growth regulator, comprises a synergistic combination of acetic acid and citric acid.

6 Claims, 2 Drawing Sheets

HERBICIDAL COMPOSITION AND USE

REFERENCE TO RELATED APPLICATION

This application is a continuation-in-part of U.S. patent application Ser. No. 08/736,683, filed Oct. 25, 1996, now U.S. Pat. No. 5,705,455, which itself is a continuation-in-part of U.S. patent application Ser. No. 08/190,201, filed Jul. 18, 1994, now U.S. Pat. No. 5,573,997.

FIELD OF INVENTION

The present invention relates to herbicidal compositions comprising synergistic mixtures of acetic acid and citric acid.

BACKGROUND TO THE INVENTION

Many herbicidal compositions exist which are effective in killing all vegetation or selective vegetation. Many are based on sophisticated chemicals, some of which are toxic to other life forms.

Acetic acid exhibits some effect as a herbicide while citric acid at high concentrations exhibits some effect as a herbicide. There have been suggestions to use acetic acid as a herbicide, e.g. DE 4 030 687 (Kast), which describes such use alone or in combination with tensides.

SUMMARY OF INVENTION

The applicant has now found that synergistic compositions of acetic acid and citric acid may be employed as a contact herbicidal composition. The essential components of the herbicidal compositions are edible materials and, hence, can be safely applied to vegetation without risk of harm to animals, including humans.

Accordingly, in one aspect, the present invention provides a novel herbicide composition which comprises an aqueous solution of a synergistic mixture of acetic acid and citric acid.

In an additional aspect of the present invention, there is provided a method of controlling post-emergent vegetative growth, which comprises applying to the vegetative growth an aqueous herbicidal composition comprising acetic acid and citric acid. The citric acid is present in the herbicidal composition in a herbicidal activity enhancing amount and the acetic acid and citric acid are present in the composition in proportions to achieve a desired degree of kill to the vegetative growth.

By itself, acetic acid does not exhibit broadleaf weeds and grasses selectivity. However, in combination with citric acid, as provided herein, it is possible to selectively control a number of annual and perennial weeds, including broadleaf weeds in established lawns and pastures.

The herbicidal composition provided herein is a contact herbicide, which may be applied by spraying above-ground portions of the weeds that it is desired to kill, providing a simple mode of administration.

The compositions of the present invention rapidly and consistently kill above-ground parts of weeds. Plant injury is observed within a few hours of application of the compositions of the invention and plant death within a few days.

The compositions of the invention may be employed to kill and control a wide variety of annual and perennial broadleaf weeds and grasses as well as mosses. Representative vegetative growth includes:

| Annual Broadleaf Weeds | Annual Grasses |
|---|---|
| Black medic | Crab grass |
| Chickweed | Foxtail spp. |
| Cinquefoil (rough) | |
| Lamb's-quarters | |
| Oxalis spp. | |
| Ragweed spp. | |
| Cocklebur | |
| Pigweed | |
| Curled Dock | |
| Fleabane spp. | |
| Russian Thistle | |
| Wild Buckwheat | |
| Perennial Broadleaf Weeds | |
| Cinquefoil (Silvery) | |
| Dandelion | |
| Plantain spp. | |
| Toadflax | |
| Tufted vetch | |
| Wild carrot | |
| Clover spp. | |
| Hawkweed spp. | |
| Annual Grasses | |
| Barnyardgrass | |
| Witchgrass | |
| Perennial Grasses | |
| Quackgrass | |
| Bluegrass | |

The compositions of the present invention further are effective as growth regulators for a variety of plants, inhibiting or stimulating growth of the plants according to the ratios of acetic acid and citric acid used. Combinations of acetic acid and citric acid show evidence of systemic activities on some species.

GENERAL DESCRIPTION OF INVENTION

Figure 1:
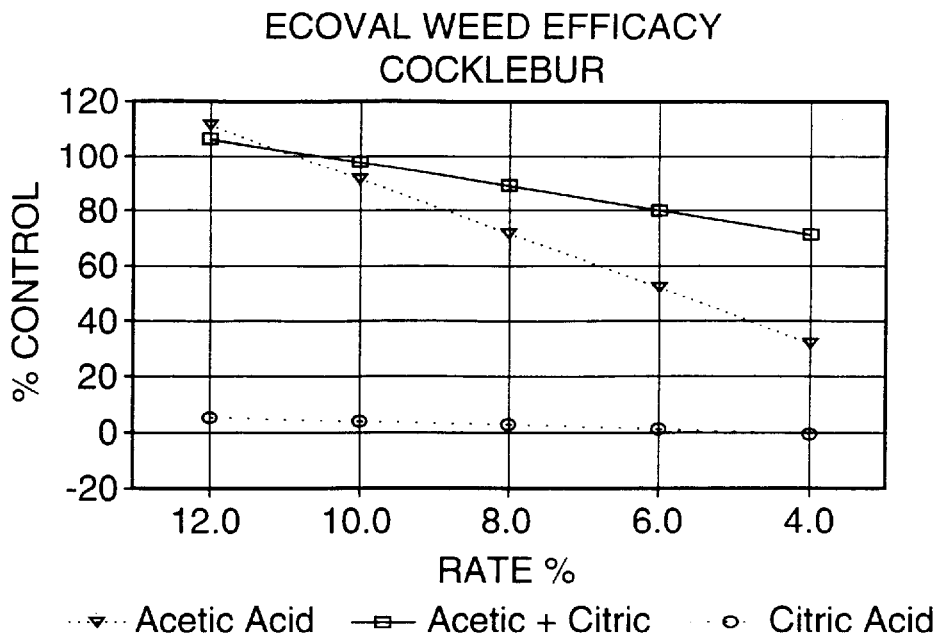
FIGS. 1 to 4 are graphical representations of rate responses to treatment of certain species with acetic acid, citric acid and mixtures.

The compositions of the invention can be formulated to effectively kill all vegetative growth, including normally hard-to-kill weeds as well as grasses, in a rapid period of time. Alternatively, the composition may be formulated as a selective herbicide, for example, to kill common lawn weeds, while leaving the grass unaffected. The composition of the invention also is useful as a defoliant.

The composition of the invention comprises a synergistic combination of acetic acid and citric acid. The acetic acid component conveniently is provided by domestic white vinegar while the citric acid is conveniently provided by lemon juice or the juice of another citrus fruit. Industrial sources of these components also may be used in formulating the compositions of the invention.

The compositions of the invention may be formulated as concentrates comprising glacial acetic acid and citric acid in the desired ratio dissolved in water, which then may be diluted to the desired strength for use. For example, a concentrate may be prepared by combining 250 g of glacial acetic acid, 125 g of citric acid (i.e. a weight ratio of acetic acid to citric acid of 2:1) with 625 g of water, to provide a concentrate containing 25 wt % acetic acid and 12.5 wt % citric acid. The composition may contain 620 g of water and 5 g (0.5 wt %) of a wetting agent. Another useful formulation of concentrate provided herein comprises:

160 g acetic acid
40 g citric acid
800 ml water

These concentrates then may be diluted by adding water to provide an aqueous herbicidal composition having the desired concentrations of acetic acid and citric acid for application to the vegetative growth to be killed.

By experimentation, it is possible to determine the degree of dilution required for specific properties of the composition for varying proportions of acetic acid and citric acid.

Although acetic acid alone exhibits some effect as a herbicide as mentioned above, the presence of small quantities of citric acid according to the present invention considerably enhances the effect. Citric acid at high concentrations exhibits some effect as a herbicide, but at the low concentrations provided herein considerably enhances the herbicidal properties of the acetic acid, thereby providing a synergistic herbicidal effect.

The weight ratio of acetic acid to citric acid in the composition of the invention may vary from about 10:1 to about 1:0.5, preferably about 4:1 to about 1:1. In general, with the presence of an increasing quantity of citric acid for the same quantity of acetic acid, there is an increasing herbicidal activity to a maximum level of such activity, at which addition of further quantities of citric acid produces no further synergistic herbicidal effect. The composition in use may contain up to about 10 wt % of acetic acid, preferably about 1 to about 5 wt. %. The composition in use may contain about 0.25 to about 5 wt % citric acid.

The herbicidal activity of the combination of acetic acid and citric acid may be enhanced further by the presence of small quantities of wetting agents to enhance the wetting ability of the compositions of the invention on the vegetative growth to which the aqueous herbicidal composition is applied. Such wetting agents preferably are edible emulsifiers.

A particularly-useful composition according to the invention comprises about 2 parts by weight of vinegar (acetic acid) and about 1 part by weight of lemon juice or other citrus fruit juice (citric acid). This composition is diluted with water to provide the composition ready for use. The degree of dilution of the composition determines whether the herbicidal composition will kill all vegetation to which it is applied and whether it is selective.

One composition which has been found useful as a total vegetation kill composition comprises:

500 mls of vinegar (acetic acid)
250 mls of lemon juice (citric acid)
750 to 1250 mls of water If the dilution is increased to about 2300 mls of water, the composition becomes a selective herbicide. Too much dilution, however, results in a composition having no herbicidal properties. For example, dilution by 5000 mls of water produces a composition which has no herbicidal response.

Another useful composition according to the invention comprises:

10 wt. % glacial acetic acid
5 wt. % citric acid
85 wt. % water.

In one preferred aspect of the present invention, there is provided an aqueous herbicidal composition for contact kill of vegetative growth, consisting essentially of:

acetic acid in an amount of from about 2 to about 10 wt % and citric acid in an amount of from about 1 to about 6 wt %, said acetic acid and citric acid being present in a synergistic weight ratio of about 1:0.1 to about 1:0.8, said composition being in fully diluted form ready to apply to post-emergent vegetative growth by spraying onto the vegetative growth. Such composition may be prepared by dilution with water from concentrate. A small amount of a wetting agent, up to about 0.5 wt %, may be present.

Where uses of the composition of the invention include exposure to high temperatures, it may be desirable to retard evaporation of the aqueous composition by incorporating therein a proportion of a suitable oil, so that the composition is in the form of an emulsion. The emulsion then is spread on the vegetative growth.

The composition of the invention is composed of natural and edible components, namely acetic acid and citric acid and hence, not only is efficacious as a herbicide, either for total or selective kill of vegetation, but is safe to use. In contrast, most herbicides require chemical synthesis and exhibit toxic side effects on animals.

The present invention is illustrated further by the following Examples:

EXAMPLE 1

This Example illustrates the synergistic effect of acetic acid and citric acid in herbicidal compositions.

Field corn, Var. Trucker's Favourite, was used as a representative test species, since the combination of acetic acid and citric acid is a non-selective herbicide and field corn is a fast growing plant, easily grown under greenhouse conditions and is representative of grass or weeds.

Field corn was direct seeded into four inch paper pots containing HYPONEX®, a soil based growing medium. One seed was planted per pot. The pots were then incubated in a greenhouse. Plants were watered at least once daily on an as-needed basis. Greenhouse temperatures ranged from 62° to 89° F. throughout the growth and test period. Seed germination occurred within 4 days of planting. Field corn was at the two leaf stage (14 days after planting) at the time of treatment.

The experiments consisted of the following compositions:

(1) Product A (acetic acid) at 10, 8.0, 6.0, 4.0 and 2.0 wt %

(2) Product B (citric acid) at 6.0, 4.8, 3.6, 2.4 and 1.2 wt %.

(3) Mixtures of Product A+Product B at five levels, at a weight ratio of acetic acid to citric acid of 1:0.6:

| A | B |
|---|---|
| 10.0 + | 6.0% |
| 8.0 + | 4.8 |
| 6.0 + | 3.6 |
| 4.0 + | 2.4 |
| 2.0 + | 1.2 |

(4) Mixtures of Product A+Product B at five levels, at various ratios of acetic acid to citric acid:

| A B | Ratio |
|---|---|
| 4.0 + 3.2% | 1:0.8 |
| 4.0 + 1.2 | 1:0.3 |
| 4.0 + 0.8 | 1:0.2 |

| A | B | Ratio |
|---|---|---|
| 4.0 + 0.4 | | 1:0.1 |

(5) Non-treated Control

Surfactant (Product C) was added to each composition, including the non-treated control, at 0.1% of the finished spray.

Six replicates were included for each composition.

The compositions were prepared in deionized water and applied to foliage using a hand-held $CO_2$ pressurized sprayer fitted with a Teejet 8001 nozzle and delivering the equivalent of 50 gallons per acre (foliar spray to near run-off). A non-treated control (water+surfactant) was included.

Applications were made using a spray pressure of 25 PSI. The spray plot area was 36"×18" and the plants were arranged within the plot area and the application applied by volume (20 ml/plot). The non-treated controls received the equivalent amount of water with surfactant but with no chemical added.

The daily greenhouse temperatures ranged from approximately 65° F. at night to 85° F. during the day. The greenhouse heating was set so that the temperature did not fall below 65° F.

Visual assessments were made of the percent necrosis of the whole plant at three days after treatment. The Barrat-Horsfall rating system was used to estimate the amount of plant injury. This rating system is a weighed, 0 to 11 rating scale with 0 being no injury and 11 being 100% injury. On the seventh day, the fresh weight of the plants were taken by cutting plants within treatment replicates at soil level. The fresh weight of each replicate was recorded.

The effect of the rate of the test composition on plant injury and fresh weight was related to the non-treated control. The Barrat-Horsfall numerical injury ratings were converted to estimated mean percent injury using a conversion table developed by Redman King and Brown, Eli Lilly and Company. All plant fresh data were entered into Quattro PRO WINDOWS (version 6.0) spreadsheet, to calculate mean values. All raw data were analyzed by analysis of variance (ANOVA 2-Way) using Quattro Pro version 6.0 program. If a significant F-Test at p=0.05 was found between the composition concentrations and the observations, then the composition mean values were separated by utilizing LSD mean separation test. $ED_{25}$ and $ED_{50}$ (Effective Dose that cause a 25 and 50 percent reduction in the parameter measured) values were determined by regression and probit analysis using Lotus 1, 2, 3 software.

The results which were obtained in this experimentation were tabulated and are presented in Tables I, II and III below. As may be seen from this data, acetic acid applied alone at 10, 8, 6, 4 and 2% showed a rate responsive effect for both plant injury and plant fresh weight. The highest rate, 10%, of acetic acid alone caused 39% plant injury and 29% reduction in plant fresh weight. An $ED_{25}$ value of 7.5% was calculated for plant injury; an $ED_{50}$ value could not be determined. For fresh weight reduction, an $ED_{25}$ value of 22.7% was extrapolated from the data. Citric acid at the rates tested, 6, 4.8, 3.6, 2.4 and 1.2%, was only weakly active causing only slight injury and no reduction in plant fresh weight. The rates tested were too low to allow an $ED_{25}$ or an $ED_{50}$ to be determined for either parameter.

When used in mixtures, acetic acid and citric acid were more effective than either alone and, therefore, synergistic. The synergistic interaction between acetic and citric acid is apparent from a comparison of rate response curves prepared from the raw data and the $ED_{25}$ values (Table III). Acetic acid alone showed an $ED_{25}$ of 7.5 for plant injury, citric acid was ineffective at the highest rate tested and the combination had an $ED_{25}$ of 2.6. This result is an increase in activity of approximately three-fold as compared to acetic acid alone at the same concentration. Similar results were obtained on the effects on fresh weight. Acetic acid alone had little effect on plant weight and an $ED_{25}$ value was extrapolated to be 22.7; the $ED_{25}$ for the mixture of acetic acid and citric acid was 9.7, a 2.5 fold increase as compared to activity of acetic acid alone.

Four mixtures of acetic acid and citric acid were tested to determine the effect of modification of their weight ratio on herbicidal activity. Acetic acid was included in each of the test mixtures at a single rate of 4.0%. Citric acid was added to produce the following weight ratios: 1:0.8, 1:0.3, 1:0.2 and 1:0.1. Under the conditions of this test, acidic acid alone at 4.0% provided only minimal activity, causing some phytotoxic effects but no effect on the fresh weight of the plants over the seven day course of the test. It is apparent that the combinations of acetic acid and citric acid are synergistic in all the ratios tested. The most effective combination found in these tests was 1 part acetic acid to 0.8 parts citric acid.

It can be seen, therefore, from these experiments that acetic acid was more effective as a herbicide when mixed with citric acid than when applied alone. Assessment of the percent control showed that synergistic action occurred for control of corn when acetic acid and citric acid were mixed. The herbicidal activity of acetic and citric acid was 2.5 to 3 times greater in combination than either material applied alone. The combination of the two materials was synergistic over a wide range of concentrations. The compositions further showed a growth regulation capacity, as seen from Table II.

EXAMPLE 2

This Example illustrates the synergistic effect on selected broadleaf and grassyweed species of acetic acid and citric acid in herbicidal compositions.

The following weed species were used for the tests described in this Example:

| Common Name | Scientific Name |
|---|---|
| Broadleaf weeds | |
| Cocklebur | *Xanthium pensylvanicum* |
| Pigweed, redroot | *Amaranthus retoflexus* |
| Grassy weed | |
| Green Foxtail | *Setaria virdis* |
| Woody Perennial | |
| Russian olive | *Elaeagnus angustifolia* |

Cocklebur, pigweed and green foxtail were direct seeded into 8×4 inch paper flats containing HYPONEX®, a soil based growing medium. Cocklebur and pigweed seed were sown into one row each; about 15 to 20 seed per row. Green foxtail was planted into a separate flat in a single row. The row was heavily seeded. The planted flats were then incubated in the greenhouse. Three year old Russian olive plants (40 plants) were purchased and placed in the greenhouse. Plants were watered at least once daily on an as needed basis. Greenhouse temperatures ranged from 65° F. to 92° F. throughout the growth and test period. The plants were grown under greenhouse conditions for 29 days before being used in the test. Seed germination was adequate and the flats were thinned to approximately 3 to 5 cocklebur and 3 to 6 pigweed in each row. Foxtail was solid seed and produced a heavy plant stand. At test initiation the cocklebur was at the 4 to 6 six leaf stage, pigweed was at the 8 to 10 leaf stage and the foxtail was at the seed head stage of development. The Russian olive plants were approximately 3 years old (16 to 20" high) and received in two gallon plastic pots.

The experiments consisted of the following compositions:

(1) Product A (acetic acid) at 12.0, 10.0, 8.0, 6.0, and 4.0%

(2) Product B (Citric acid) at 7.2, 6.0, 4.3, 3.6 and 2.4%

(3) Mixture of Product A+Product B at five levels, maintaining a ratio of acetic acid:citric acid of 1:0.6:

| A | B |
|---|---|
| 12.0 + 7.2 | |
| 10.0 + 6.0% | |
| 8.0 + 4.8 | |
| 6.0 + 3.6 | |
| 4.0 + 2.4 | |

(4) Mixture of Product A and Product B at 1 part mixture: 3 parts water (6.25%+3.1% acetic acid:citric acid).

(5) Non-treated Control

Surfactant was added to each treatment, including the non-treated control at 0.1% of the finished spray. Surfactant was not added to the Product 4 treatment.

Two replicate flats or pots were included for each treatment rate. The compositions were prepared in deionized water and applied to foliage using a hand held $CO_2$ pressurized sprayer fitted with a Teejet 8001 nozzle and delivering the equivalent of 50 gallons per acre (foliar spray to near run-off). A non-treated control (water+surfactant) was included.

Applications were made using a spray pressure of 25 PSI. The spray plot area was 36"×18" and the plants were arranged within the plot area and the application applied by volume (20 ml/plot). The non-treated controls received the equivalent amount of water with surfactant but with no chemical added.

The daily greenhouse temperatures ranged from approximately 65° F. at night to 92° F. during the day. The greenhouse heating was set so that the temperature did not fall below 65° F.

Visual assessments were made of the percent necrosis of the whole plant at three days after treatment. The Barrat-Horsfall rating system was used to estimate the amount of plant injury.

The effect of the rate of the test compound on plant injury was related to the non-treated control. The Barrat-Horsfall numerical injury ratings were converted to estimated mean percent injury using a conversion table developed by Redman King and Brown, Eli Lilly and Company. All plant injury data were entered into Quattro PRO WINDOWS (version 6.0) spreadsheet, to calculate treatment means. All raw data were analyzed by analysis of variance (ANOVA 2-Way) using Quattro Pro version 6.0 program. If a significant F-Test at p=0.05 was found between the treatment concentrations and the observations, then the treatment means were separated by utilizing LSD mean separation test. $ED_{25}$ and $ED_{50}$ values were determined by regression and probit analysis using Lotus 1,2,3 software.

Acetic acid applied alone at 12, 10, 8, 6, and 4% showed a rate responsive effect for plant injury (herbicidal activity) on all of the weed species (Tables IV, V, VI and VII).

Figure 2:
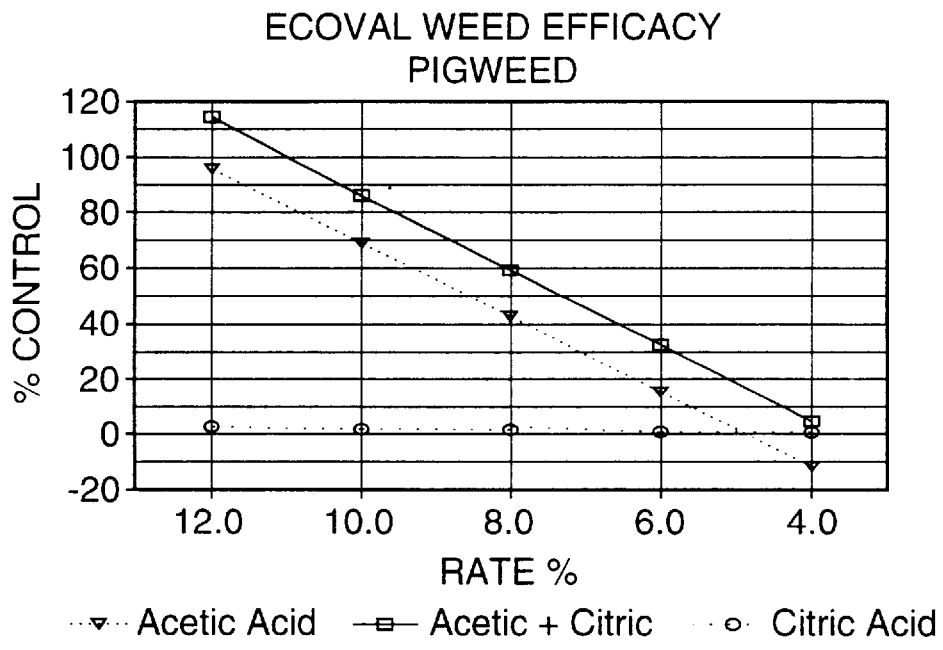
Figure 3:
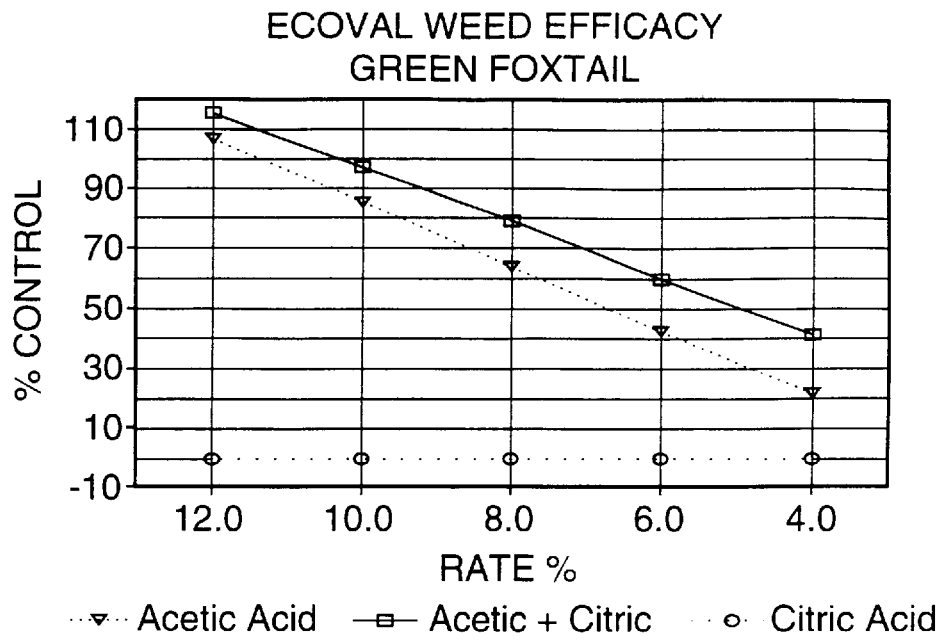
Figure 4:
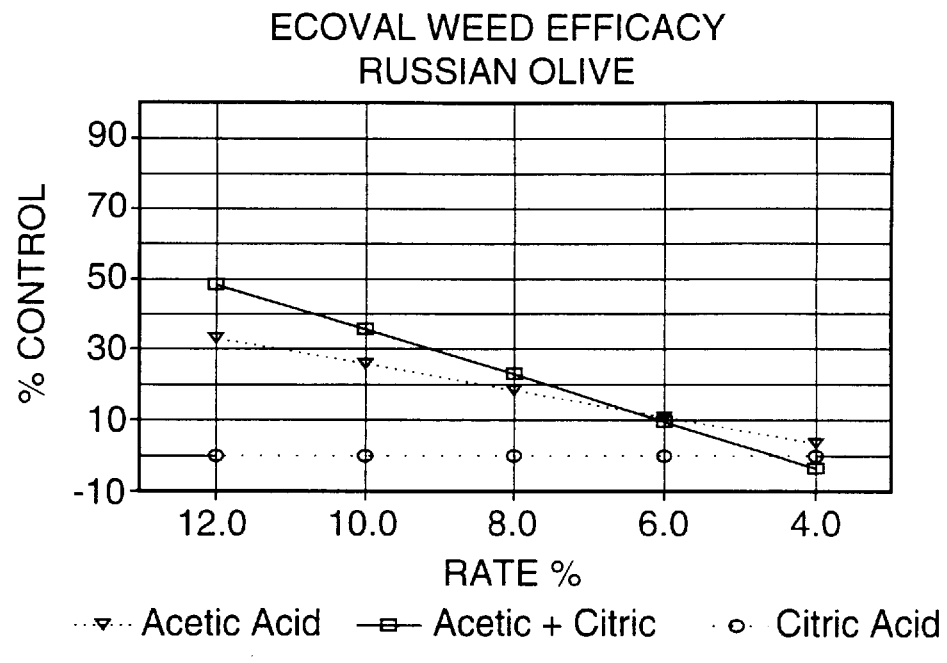

Citric acid at the rates tested, 6, 4.8, 3.6, 2.4 and 1.2%, was inactive or only weakly active. Citric acid caused only slight injury to pigweed and cocklebur and no injury to green foxtail or Russian olive. When used in mixtures, acetic acid and citric acid were more effective than either alone and, therefore, synergistic. The synergistic interaction between acetic and citric acid is apparent from the comparison of the rate response curves (FIGS. 1, 2, 3 and 4) and the $ED_{50}$ values (Table VIII). An $ED_{50}$ value could not be determined for the perennial species, Russian olive because of the lower activity of ECO-N-SELECT against this species. For the annual weed species, the increase in activity of the mixture of acetic and citric acid over acetic acid alone is in the range of approximately 20 to 40% (at the $ED_{50}$ values).

Results from these experiments indicate that acetic acid was more effective as a herbicide when mixed with citric acid then when applied alone. Assessment of the percent control and regression lines showed that synergistic action occurred for control of all weed species tested when acetic and citric acids were mixed. The herbicidal activity was 20 to 40% greater (when measured at the $ED_{50}$ value) in combination than either material applied alone. The combination of the two materials is synergistic over a wide range of concentrations as evidenced by the regression response lines.

SUMMARY OF DISCLOSURE

In summary of this disclosure, the present invention relates to a novel herbicidal composition comprising synergistic combinations of acetic acid and citric acid, most conveniently provided by vinegar and lemon juice, which are diluted with water to provide the desired herbicidal properties. Modifications are possible within the scope of this invention.

TABLE I

SYNERGISTIC HERBICIDAL EFFECTS OF MIXTURES OF ACETIC AND CITRIC ACID. PHYTOTOXICITY RATING OF CORN PLANTS THREE DAYS AFTER TREATMENT

| TREATMENT | RATE (%) | AVE. % PHYTO † |
|---|---|---|
| ACETIC ACID | 10.0 | 45 |
| | 8.0 | 10 |
| | 6.0 | 4 |
| | 4.0 | 3 |
| | 2.0 | 2 |
| CITRIC ACID | 6.0 | 2 |
| | 4.8 | 2 |
| | 3.6 | 2 |
| | 2.4 | 1 |
| | 1.2 | 0 |
| ACETIC + CITRIC | 10.0 + 6.0 | 96 |
| | 8.0 + 4.8 | 79 |
| | 6.0 + 3.6 | 53 |
| | 4.0 + 2.4 | 21 |
| | 2.0 + 1.2 | 4 |
| ACETIC + CITRIC | 4.0 + 3.2 | 41 |
| | 4.0 + 1.2 | 24 |
| | 4.0 + 0.8 | 14 |
| | 4.0 + 0.4 | 13 |
| CONTROL | 0.0 | 0 |

† Injury rated, using Barrat-Horsfall System, on a 1 to 11 scale with 0 being no injury and 11 being 100% injury.

TABLE II

SYNERGISTIC HERBICIDAL EFFECTS OF

MIXTURES OF ACETIC AND CITRIC ACID.
FRESH WEIGHT OF CORN PLANTS SEVEN
DAYS AFTER TREATMENT

| TREATMENT | RATE (%) | AVE. WT (g) | STD DEV |
|---|---|---|---|
| ACETIC ACID | 10.0 | 1.57 | 0.51 |
|  | 8.0 | 2.65 | 0.58 |
|  | 6.0 | 1.82 | 0.48 |
|  | 4.0 | 2.02 | 0.74 |
|  | 2.0 | 2.20 | 0.39 |
| CITRIC ACID | 6.0 | 2.57 | 0.48 |
|  | 4.8 | 2.25 | 0.50 |
|  | 3.6 | 2.57 | 0.51 |
|  | 2.4 | 2.22 | 0.33 |
|  | 1.2 | 2.70 | 0.53 |
| ACETIC + CITRIC | 10.0 + 6.0 | 0.82 | 0.19 |
|  | 8.0 + 4.8 | 2.22 | 0.42 |
|  | 6.0 + 3.6 | 2.73 | 0.73 |
|  | 4.0 + 2.4 | 2.92 | 1.25 |
|  | 2.0 + 1.2 | 3.15 | 1.21 |
| ACETIC + CITRIC | 4.0 + 3.2 | 2.65 | 0.64 |
|  | 4.0 + 1.2 | 2.55 | 0.69 |
|  | 4.0 + 0.8 | 2.63 | 0.88 |
|  | 4.0 + 0.4 | 3.67 | 1.56 |
| CONTROL | 0.0 | 2.22 | 0.39 |

TABLE III

PLANT INJURY AND FRESH WEIGHT,
$ED_{25}$ AND $ED_{50}$ IN % a.i.

| TREATMENT/PARAMETER | $ED_{25}$ | $ED_{50}$ |
|---|---|---|
| Acetic Acid Alone |  |  |
| Plant Injury | 7.5 | ND |
| Fresh Weight | 22.7 † | ND |
| Citric Acid Alone |  |  |
| Plant Injury | ND | ND |
| Fresh Weight | ND | ND |
| Acetic + Citric |  |  |
| Plant Injury | 2.6 | 5.3 |
| Fresh Weight | 5.3 | 10.5 |

ND = Not Determined
† = Extrapolated Value

TABLE IV

SYNERGISTIC HERBICIDAL EFFECTS OF MIXTURES OF
ACETIC AND CITRIC ACID. PHYTOTOXICITY RATING OF
COCKLEBUR SEVEN DAYS AFTER TREATMENT

| TREATMENT | RATE (%) | AVE. % PHYTO † |
|---|---|---|
| ACETIC ACID | 12.0 | 98.8 |
|  | 10.0 | 100.0 |
|  | 8.0 | 62.5 |
|  | 6.0 | 85.9 |
|  | 4.0 | 4.7 |
| CITRIC ACID | 7.2 | 4.7 |
|  | 6.0 | 3.5 |
|  | 4.8 | 2.3 |
|  | 3.6 | 0.0 |
|  | 2.4 | 0.0 |
| ACETIC + CITRIC | 12.0 + 7.2 | 100.0 |
|  | 10.0 + 6.4 | 100.0 |
|  | 8.0 + 4.8 | 94.1 |
|  | 6.0 + 3.6 | 85.9 |
|  | 4.0 + 2.4 | 62.5 |
| ECO-N-SELECT# | 7.5 + 3.8 | 91 |
| CONTROL | 0.0 | 0 |

† Injury rated, using Barrat-Horsfall System, on a 1 to 11 scale with 0 being no injury and 11 being 100% injury.
Applied at the recommended field use rate of 300 ml ECO-N-SELECT + 700 ml water.

TABLE V

SYNERGISTIC HERBICIDAL EFFECTS OF MIXTURES OF
ACETIC AND CITRIC ACID. PHYTOTOXICITY RATING OF
PIGWEED SEVEN DAYS AFTER TREATMENT

| TREATMENT | RATE (%) | AVE. % PHYTO † |
|---|---|---|
| ACETIC ACID | 12.0 | 90.6 |
|  | 10.0 | 96.5 |
|  | 8.0 | 19.0 |
|  | 6.0 | 3.5 |
|  | 4.0 | 2.3 |
| CITRIC ACID | 7.2 | 2.3 |
|  | 6.0 | 2.3 |
|  | 4.8 | 1.1 |
|  | 3.6 | 0.0 |
|  | 2.4 | 0.0 |
| ACETIC + CITRIC | 12.0 + 7.2 | 100.0 |
|  | 10.0 + 6.4 | 97.7 |
|  | 8.0 + 4.8 | 76.6 |
|  | 6.0 + 3.6 | 14.1 |
|  | 4.0 + 2.4 | 4.7 |
| ECO-N-SELECT# | 7.5 + 3.8 | 91 |
| CONTROL | 0.0 | 0 |

† Injury rated, using Barrat-Horsfall System, on a 1 to 11 scale with 0 being no injury and 11 being 100% injury.
Applied at the recommended field use rate of 300 ml ECO-N-SELECT + 700 ml water.

TABLE VI

SYNERGISTIC HERBICIDAL EFFECTS OF MIXTURES OF
ACETIC AND CITRIC ACID. PHYTOTOXICITY RATING OF
GREEN FOXTAIL SEVEN DAYS AFTER TREATMENT

| TREATMENT | RATE (%) | AVE. % PHYTO \ |
|---|---|---|
| ACETIC ACID | 12.0 | 97.7 |
|  | 10.0 | 96.5 |
|  | 8.0 | 62.5 |
|  | 6.0 | 51.0 |
|  | 4.0 | 14.1 |
| CITRIC ACID | 7.2 | 0.0 |
|  | 6.0 | 0.0 |
|  | 4.8 | 0.0 |
|  | 3.6 | 0.0 |
|  | 2.4 | 0.0 |
| ACETIC + CITRIC | 12.0 + 7.2 | 97.7 |
|  | 10.0 + 6.4 | 97.7 |
|  | 8.0 + 4.8 | 97.7 |
|  | 6.0 + 3.6 | 90.6 |
|  | 4.0 + 2.4 | 9.4 |
| ECO-N-SELECT# | 7.5 + 3.8 | 93.0 |
| CONTROL | 0.0 | 0 |

† Injury rated, using Barrat-Horsfall System, on a 1 to 11 scale with 0 being no injury and 11 being 100% injury.
Applied at the recommended field use rate of 300 ml ECO-N-SELECT + 700 ml water.

TABLE VII

SYNERGISTIC HERBICIDAL EFFECTS OF MIXTURES OF
ACETIC AND CITRIC ACID. PHYTOTOXICITY RATING OF
RUSSIAN OLIVE SEVEN DAYS AFTER TREATMENT

| TREATMENT | RATE (%) | AVE. % PHYTO † |
|---|---|---|
| ACETIC ACID | 12.0 | 38 |
| | 10.0 | 19 |
| | 8.0 | 19 |
| | 6.0 | 10 |
| | 4.0 | 5 |
| CITRIC ACID | 7.2 | 0.0 |
| | 6.0 | 0.0 |
| | 4.8 | 0.0 |
| | 3.6 | 0.0 |
| | 2.4 | 0.0 |
| ACETIC + CITRIC | 12.0 + 7.2 | 50 |
| | 10.0 + 6.4 | 38 |
| | 8.0 + 4.8 | 19 |
| | 6.0 + 3.6 | 5 |
| | 4.0 + 2.4 | 9.4 |
| ECO-N-SELECT# | 7.5 + 3.8 | 15 |
| CONTROL | 0.0 | 0 |

† Injury rated, using Barrat-Horsfall System, on a 1 to 11 scale with 0 being no injury and 11 being 100% injury.
Applied at the recommended field use rate of 300 ml ECO-N-SELECT + 700 ml water.

TABLE VIII

EFFECT DOSAGE VALUES AT $ED_{25}$ AND $ED_{50}$ IN % ACTIVE INGREDIENT FOR COCKLEBUR, PIGWEED AND GREEN FOXTAIL. SEVEN DAY DATA.

| TREATMENT/Weed Species | $ED_{25}$ | $ED_{50}$ |
|---|---|---|
| Acetic Acid Alone | | |
| Cocklebur | 3.2 | 5.8 |
| Pigweed | 5.6 | 8.4 |
| Gr. Foxtail | 3.6 | 6.3 |
| Citric Acid Alone | | |
| Cocklebur | ND | ND |
| Pigweed | ND | ND |
| Gr. Foxtail | ND | ND |
| Acetic + Citric | | |
| Cocklebur | 0.7 | 3.8 |
| Pigweed | 4.3 | 6.8 |
| Gr. Foxtail | 2.4 | 5.0 |

ND = Not Determined > 7.2% (highest rate tested)

What I claim is:

1. A method of controlling post-emergent vegetative growth, which comprises applying to said vegetative growth an aqueous herbicidal composition comprising acetic acid and citric acid, said citric acid being present in a herbicidal activity enhancing amount and said acetic acid and citric acid being present in proportions sufficient to achieve a complete kill of the vegetative growth to which the composition is applied.

2. A method of controlling post-emergent vegetative growth, which comprises applying to said vegetative growth an aqueous herbicidal composition comprising acetic acid and citric acid, said citric acid being present in a herbicidal activity enhancing amount and said acetic acid and citric acid being present in proportions sufficient to achieve a selective kill of certain of the vegetative growth to which the composition is applied.

3. The method of claim 1 or 2 wherein said herbicidal composition is applied to the vegetative growth by spraying.

4. The method of claim 1 or 2 wherein said aqueous herbicidal composition consists essentially of:
   acetic acid in an amount of from about 2 to about 10 wt %,
   citric acid in an amount of from about 1 to about 6 wt %,
   said acetic acid and citric acid being present in a
   synergistic weight ratio of about 1:0.1 to about 1:0.8
   and in said proportions,
   said composition being in fully diluted form ready to apply to the post-emergent vegetative growth.

5. The method of claim 4 comprising the further steps of providing said aqueous herbicidal composition as a concentrate and diluting said concentrate with water prior to said applying step.

6. The method of claim 4 wherein said aqueous herbicidal composition further contains up to about 0.5 wt % of a wetting agent.

* * * * *